United States Patent
Ieda et al.

(10) Patent No.: US 7,416,649 B2
(45) Date of Patent: Aug. 26, 2008

(54) OXYGEN CONCENTRATION DETECTION SYSTEM AND VEHICLE CONTROL SYSTEM HAVING THE SAME

(75) Inventors: Norikazu Ieda, Aichi (JP); Yuji Oi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 910 days.

(21) Appl. No.: 10/802,716

(22) Filed: Mar. 18, 2004

(65) Prior Publication Data
US 2004/0222094 A1    Nov. 11, 2004

(30) Foreign Application Priority Data
Mar. 18, 2003    (JP)    ............................... 2003-74362

(51) Int. Cl.
*G01N 27/41*    (2006.01)
(52) U.S. Cl. ........................ 204/401; 204/425; 73/23.32
(58) Field of Classification Search ................ 204/401, 204/424, 425; 205/784.5, 785; 73/23.32
See application file for complete search history.

(56) References Cited

U.S. PATENT DOCUMENTS

| | | | |
|---|---|---|---|
| 4,765,880 A | | 8/1988 | Hayakawa et al. |
| 4,819,602 A | * | 4/1989 | Mieno et al. ................ 123/688 |
| 5,298,865 A | | 3/1994 | Denz et al. |
| 5,709,198 A | * | 1/1998 | Sagisaka et al. ............. 123/684 |
| 6,099,717 A | * | 8/2000 | Yamada et al. ........... 205/784.5 |
| 2002/0175086 A1 | | 11/2002 | Nakamichi et al. |

FOREIGN PATENT DOCUMENTS

| EP | 1 134 580 A1 | 9/2001 |
|---|---|---|
| JP | 3-272452 | 12/1991 |
| JP | 5-21499 | 3/1993 |
| JP | 2002-257772 | 9/2002 |
| JP | 2003-97342 | 4/2003 |

OTHER PUBLICATIONS

European Search Report for EP 04 29 0740 dated Jul. 26, 2004.

* cited by examiner

*Primary Examiner*—Kaj K Olsen
(74) *Attorney, Agent, or Firm*—Sughrue Mion, PLLC

(57) ABSTRACT

An oxygen concentration detection system including an oxygen sensor which outputs a plurality of types of measurement signals and anomaly detection means and modification means. The anomaly detection means detects a sensor anomaly by determining whether the respective levels of the plurality of types of measurement signals fall within predetermined ranges. When a sensor anomaly is not detected, the modification means outputs the plurality of types of measurement signals as is. When a sensor anomaly is detected, the modification means outputs at least one of the plurality of types of measurement signals at a level outside the corresponding range within which the level of the measurement signal varies in a normal state.

16 Claims, 8 Drawing Sheets

Fig. 3

| VVS | VIP | VRPVS | ANOMALY JUDGMENT IN LEAN REGION | ANOMALY JUDGMENT IN NON-LEAN REGION |
|---|---|---|---|---|
| N | N | N | NORMAL | NORMAL |
| N | N | L | OTHER ANOMALY | OTHER ANOMALY |
| N | N | H | OTHER ANOMALY | OTHER ANOMALY |
| N | N | HH | OTHER ANOMALY | OTHER ANOMALY |
| N | L | N | Ip+ BREAKAGE | NORMAL |
| N | L | L | OTHER ANOMALY | OTHER ANOMALY |
| N | L | H | COM BREAKAGE | OTHER ANOMALY |
| N | L | HH | | OTHER ANOMALY |
| N | LL | N | OTHER ANOMALY | NORMAL |
| N | LL | L | OTHER ANOMALY | OTHER ANOMALY |
| N | LL | H | OTHER ANOMALY | OTHER ANOMALY |
| N | LL | HH | GROUND-SIDE SHORT CIRCUIT OF Ip+ OR COM | GROUND-SIDE SHORT CIRCUIT OF Ip+ OR COM |
| L | N | N | OTHER ANOMALY | OTHER ANOMALY |
| L | N | L | OTHER ANOMALY | OTHER ANOMALY |
| L | N | H | OTHER ANOMALY | OTHER ANOMALY |
| L | N | HH | OTHER ANOMALY | OTHER ANOMALY |
| L | L | N | OTHER ANOMALY | OTHER ANOMALY |
| L | L | L | OTHER ANOMALY | OTHER ANOMALY |
| L | L | H | OTHER ANOMALY | OTHER ANOMALY |
| L | L | HH | OTHER ANOMALY | OTHER ANOMALY |
| L | LL | N | OTHER ANOMALY | OTHER ANOMALY |
| L | LL | L | OTHER ANOMALY | OTHER ANOMALY |
| L | LL | H | OTHER ANOMALY | OTHER ANOMALY |
| L | LL | HH | BATTERY-SIDE SHORT CIRCUIT OF Vs+, Ip+, OR COM | BATTERY-SIDE SHORT CIRCUIT OF Vs+, Ip+, OR COM |
| H | N | N | OTHER ANOMALY | OTHER ANOMALY |
| H | N | L | OTHER ANOMALY | OTHER ANOMALY |
| H | N | H | OTHER ANOMALY | OTHER ANOMALY |
| H | N | HH | OTHER ANOMALY | OTHER ANOMALY |
| H | L | N | OTHER ANOMALY | OTHER ANOMALY |
| H | L | L | OTHER ANOMALY | OTHER ANOMALY |
| H | L | H | OTHER ANOMALY | OTHER ANOMALY |
| H | L | HH | OTHER ANOMALY | OTHER ANOMALY |
| H | LL | N | OTHER ANOMALY | OTHER ANOMALY |
| H | LL | L | OTHER ANOMALY | OTHER ANOMALY |
| H | LL | H | OTHER ANOMALY | OTHER ANOMALY |
| H | LL | HH | Vs+ BREAKAGE OR GROUND-SIDE SHORT CIRCUIT OF Vs+ | Vs+ BREAKAGE OR GROUND-SIDE SHORT CIRCUIT OF Vs+ |

Fig. 7

| Vs+ voltage | Comparator 1 | Comparator 2 | NOR | SW0 | SW1 | SW2 | VVS Output |
|---|---|---|---|---|---|---|---|
| High | H | L | L | Off | On | Off | 5V |
| Normal | L | L | H | On | Off | Off | A(Vs) + B |
| Low | L | H | L | Off | Off | On | 0V |

OXYGEN CONCENTRATION DETECTION SYSTEM AND VEHICLE CONTROL SYSTEM HAVING THE SAME

BACKGROUND OF THE INVENTION

1. Field of the Invention

The present invention relates to an oxygen concentration detection system and to a vehicle control system which includes the same so as to detect the air-fuel ratio of an internal combustion engine such as a gasoline engine or a diesel engine. More particularly, the present invention relates to an oxygen concentration detection system which can report anomalous conditions of a plurality of types without an increase in the number of signal lines, as well as to a vehicle control system including the same.

2. Description of the Related Art

In a known vehicle control system for an internal combustion engine such as a gasoline engine or a diesel engine, an oxygen sensor is disposed in an exhaust system, and the quantity of fuel supplied to the engine is feedback-controlled in accordance with the sensor output such that the air fuel ratio approaches a target value, whereby CO, $NO_x$, HC, etc. in exhaust gas are reduced.

Know oxygen sensors used in such feedback control include a λ sensor whose output abruptly changes in the vicinity of the theoretical air fuel ratio, and a full range air-fuel-ratio sensor whose output continuously changes from a lean region to a rich region. The full range air-fuel-ratio sensor is advantageous in that it can improve the accuracy of the feedback control as compared with that of the λ sensor.

The full range air-fuel-ratio sensor includes two opposed cells formed of an oxygen-ion conductive solid electrolyte. One of the cells is a pump cell which pumps oxygen out of a clearance (measurement chamber) between the cells and pumps oxygen into the clearance. The other cell is an oxygen-partial-pressure detection cell which produces a voltage corresponding to the difference between a reference oxygen concentration and the oxygen concentration in the measurement chamber. These cells are controlled by means of a control circuit. In the full range air-fuel-ratio sensor, the pump cell is operated such that the output of the oxygen-partial-pressure detection cell is maintained constant, and the oxygen concentration is detected on the basis of the magnitude of current flowing though the pump cell. The operation principle of the full range air-fuel-ratio sensor is described in detail in Japanese Patent Application Laid-Open (kokai) No. 62-148849 of the present inventors.

Meanwhile, an anomaly detection method for an air-fuel-ratio sensor adapted to detect whether or not the air-fuel-ratio sensor operates normally is disclosed, for example, in Japanese Patent Application Laid-Open (kokai) No. 3-272452, also of the present inventors, entitled "Anomaly Diagnosis Method for Air-Fuel-Ratio Sensor".

3. Problems Solved by the Invention:

However, in JPA No. 3-272452, since an anomaly is judged on the basis of a variation range of voltage of an oxygen detection cell, the cell is judged to be anomalous even when the voltage temporarily exceeds the range as a result of, for example, noise in the control circuit. Therefore, the anomaly judgment may be erroneous. In order to eliminate the noise problem, a signal line for reporting the occurrence of an anomaly may be added. In this case, the wiring becomes complex, and an input port or the like must be added on the side where a report of occurrence of anomaly is received, leading to increased cost. Moreover, when only one signal line is provided for reporting the occurrence of an anomaly, only simple information can be provided.

SUMMARY OF THE INVENTION

It is therefore an object of the present invention to provide an oxygen concentration detection system which can report the occurrence of anomaly in an oxygen sensor by use of a simple configuration, as well as a vehicle control system including the oxygen concentration detection system.

According to a first aspect, the present invention provides an oxygen concentration detection system 100 which comprises an oxygen sensor 1. The oxygen sensor 1 comprises a sensor element 10 including a combination of an oxygen pump cell 14 and an oxygen-partial-pressure detection cell 24; and a control circuit 50 connected to the sensor element 10 via wiring lines 41, 42, and 43 adapted to control the oxygen pump cell 14 such that the output voltage of the oxygen-partial-pressure detection cell 24 is maintained at a predetermined value. The control circuit 50 may also perform other functions. The oxygen sensor 1 detects concentration of oxygen contained in a gas to be measured having an oxygen concentration within a predetermined range. The oxygen concentration detection system 100 outputs signals 81 of a plurality of types, including a signal 81b corresponding to a magnitude of current flowing through the oxygen pump cell 14, a signal 81c corresponding to an electric potential of the oxygen-partial-pressure detection cell 24, and a signal 81a corresponding to a resistance of the oxygen-partial-pressure detection cell 24. The oxygen concentration detection system 100 is characterized by comprising: anomaly detection means 58 for detecting a sensor anomaly by determining whether or not at least one of respective levels of signals 581, 582, and 583 which represent electric potentials at different portions of the sensor element 10, the wiring lines 41, 42, and 43, and the control circuit 50 falls within a predetermined range; modification means 58d for issuing a first instruction when the anomaly detection means 58 does not detect any anomaly, the first instruction indicating non-detection of anomaly, and for issuing a second instruction when the anomaly detection means 58 detects a sensor anomaly, the second instruction corresponding to the detected anomaly; and output means 83 for through-outputting the measurement signals 81 when the modification means 58d outputs the first instruction signal and for outputting at least a selected one of the measurement signals 81 when the modification means 58d outputs the second instruction signal, the selected measurement signal being modified to have a level outside the corresponding range within which the level of the selected measurement signal varies in a normal state. The term "through-output" means that an output from the sensor or resulting output from the control circuit is output directly without modification.

According to the present invention, when normal signals are output to the plurality of signal lines, the oxygen concentration detection system reports that the voltages of the signals are normal voltages falling within predetermined respective ranges, and when an anomaly occurs, the oxygen concentration detection system reports the occurrence of an anomaly by changing the voltage of a selected signal to fall outside the corresponding range.

This configuration eliminates the necessity of providing an additional signal line for reporting an anomalous state, reduces the degree of complication, and enhances reliability. This configuration also enables judgment of an anomaly state to be performed simultaneously with confirmation of validity of a signal of a relevant signal line, whereby the load imposed on an engine control unit (ECU) can be reduced.

According to a first aspect of the present invention, the oxygen sensor is judged to be anomalous when one of the signal lines outputs a voltage which is not output in a normal state; and the type of anomaly can be transmitted by combining the levels of the respective signal lines in various manners. Thus, addition of an extra signal line is not required, the degree of complication of routing of wiring lines can be reduced, and detection failure, which would otherwise occur due to breakage, etc., of an added signal line, does not occur. Moreover, since the existing signals and an anomaly detection signal do not overlap in terms of output range, no problem arises in detection of air fuel ratio.

According to a second aspect, the present invention provides an oxygen concentration detection system 100 wherein the anomaly detection means 58 detects an anomaly of at least one of the oxygen pump cell 14, the oxygen-partial-pressure detection cell 24, the control circuit 50, and the wiring lines 41, 42, and 43.

According to the second aspect of the present invention, an anomaly of the oxygen concentration detection system can be detected, while a portion(s) of the sensor element, the control circuit, and the signal wiring lines is specified.

According to a third aspect, the present invention provides an oxygen concentration detection system 100 wherein line signals including signal 83c (VCC5) having a level falling outside the predetermined range within which the level of the measurement signal varies in a normal state is output by use of a signal line 81a, 81b and/or 81c through which the measurement signal 81 of a level falling within the predetermined range is output.

According to the third aspect of the present invention, since the signal having a level falling outside the predetermined range within which the level of the measurement signal varies in a normal state; i.e., an error signal, is output as an anomalous detection signal, by use of a signal line for a measurement signal, such that an additional signal line is not required.

According to a fourth aspect, the present invention provides an oxygen concentration detection system 100 wherein the output means 83 includes switches 83a and 83b for switching their connection states in accordance with an instruction from the modification means 58d, and a constant voltage source 83d, wherein when the second instruction indicative of anomaly is output from the modification means 58d, the constant voltage power source 83d is connected, through a switching operation of the switches, to a signal line to which a selected one of the measurement signals 81 is output, to thereby change the level of the selected measurement signal to a level falling outside the predetermined range within which the level of the measurement signal varies in a normal state.

According to the fourth aspect of the present invention, a constant voltage source for generating a voltage serving as an anomaly detection signal is disposed in the control circuit, and switches are provided for selectively outputting a normal signal or the anomaly detection signal on the basis of the instruction from the modification means, whereby a signal indicative of an anomaly can be easily output, and a complicated amplification circuit for output switching is not required.

According to a fifth aspect, the present invention provides an oxygen concentration detection system 100 wherein when a sensor anomaly occurs, the anomaly detection means 58 determines that the level of one of the signals 58l, 58l, and 58l which represent electric potentials at different portions of the sensor element 10, the wiring lines 41, 42, and 43, and the control circuit 50 falls outside the corresponding predetermined range, and outputs a predetermined anomaly detection signal 58a1, 58b1, 58c1 in accordance with the type and/or level of the signal whose level falls outside the predetermined range. The modification means 58d issues, in accordance with the anomaly detection signal 58a1, 58b1, 58c1 output from the anomaly detection means 58, a control signal 58e for specifying a signal which is to be output at a level falling outside the corresponding range within which the level of the signal varies in a normal state. The output means 83 outputs, on the basis of the control signal 58e output from the modification means 58d, at least one of the signals 81 specified by the modification means 58d, at a predetermined level falling outside the corresponding range within which the level of the signal varies in a normal state, whereby the location and/or state of the anomaly of the sensor element 10 is reported.

According to the fifth aspect of the present invention, in the control circuit, a predetermined output(s) from the sensor element is converted to a predetermined voltage signal, and anomaly detection is performed by use of the signal. Upon anomaly detection, the measurement signal is replaced with an anomaly detection signal having a predetermined level, whereby an anomalous state is reported. Therefore, an anomalous location and/or state of an anomaly of the sensor element is quickly transferred into the ECU, whereby the state of an anomaly can be quickly detected.

According to a sixth aspect, the present invention provides an oxygen concentration detection system 100 wherein the anomaly detection means 58, the modification means 58d, and the output means 83 are provided in the control circuit 50 of the sensor element 10.

According to the sixth aspect of the present invention, since the anomaly detection means, the modification means, and the output means are provided in the sensor control circuit of the sensor element, the circuit and processes within the ECU can be simplified.

According to a seventh aspect of the present invention, the oxygen sensor 1 includes a heater 61 for heating the sensor element 10; and a heater control circuit 60 for controlling electric power supplied to the heater 61 such that the sensor element 10 is maintained at a predetermined temperature.

Since the oxygen sensor includes a heater and a heater control circuit therefor, the oxygen sensor can be quickly activated, and in particular, at startup of an engine, the oxygen sensor can be quickly heated to the predetermined temperature. In addition, an anomaly of the sensor can be quickly detected after startup of the engine.

According to an eighth aspect, the present invention provides an oxygen concentration detection system 100 wherein when an anomaly is detected in the signals 58l, 58l, and 58l representing the electric potentials at the different locations, the output means 83 changes the level of a measurement signal corresponding to the resistance of the oxygen-partial-pressure detection cell 24 to a level falling outside the predetermined range in which the level of the measurement signal varies in a normal state.

According to the eighth aspect of the present invention, the switch which effects changeover between a normal signal and an anomaly detection signal in accordance with an instruction from the modification means is provided only in the signal line for outputting the measurement signal corresponding to the resistance of the oxygen-partial-pressure detection cell. Thus, the number of switches can be reduced to one, thereby simplifying the control circuit.

According to a ninth aspect, the present invention provides a vehicle control system 900, comprising an oxygen sensor 1 which comprises a sensor element 10 including a combination of an oxygen pump cell 14 and an oxygen-partial-pressure detection cell 24; a control circuit 50 connected to the sensor element 10 via wiring lines 41, 42, and 43 and adapted to control the oxygen pump cell 14 such that the output voltage of the oxygen-partial-pressure detection cell 24 is maintained at a predetermined value. The control circuit 50 may also perform additional functions. The oxygen sensor 1 detects the concentration of oxygen contained in a gas to be measured having an oxygen concentration within a predetermined range. The vehicle control system 900 further comprises: anomaly detection means 58 for detecting sensor anomaly by determining whether or not at least one of respective levels of signals 581, 582, and 583 which represent electric potentials at different portions of the sensor element 10, the wiring lines 41, 42, and 43, and the control circuit 50 falls within a predetermined range; modification means 58d for issuing a first instruction when the anomaly detection means 58 does not detect any anomaly, a first instruction showing non-detection of an anomaly, and for issuing a second instruction when the anomaly detection means 58 detects a sensor anomaly, a second instruction corresponding to the detected anomaly; output means 83 for through-outputting the measurement signals 81 when the modification means 58d outputs the first instruction signal and for outputting at least a selected one of the measurement signals 81 when the modification means 58d outputs the second instruction signal, the selected measurement signal being modified to have a level outside the corresponding range within which the level of the selected measurement signal varies in a normal state; and anomaly judgment means 80 for judging whether or not the vehicle control system 900 detects an anomalous condition, on the basis of measurement signals 81 of a plurality of types, including a signal 81b corresponding to a magnitude of current flowing through the oxygen pump cell 14, a signal 81c corresponding to an electric potential of the oxygen-partial-pressure detection cell 24, and a signal 81a corresponding to a resistance of the oxygen-partial-pressure detection cell 24.

According to the ninth aspect of the present invention, since anomaly judgment means is incorporated in the vehicle control system, an additional signal line is not required, and the degree of complication of routing of wire lines can be reduced. Moreover, since the existing signals and the anomaly detection signals do not overlap in terms of output range, no problem arises in detection of air fuel ratio. Furthermore, there is no interference stemming from noise, etc., and thus, anomaly judgment for the vehicle control system can be performed with high accuracy.

According to a tenth aspect, the present invention provides a vehicle control system 900, wherein the anomalous judgment means 80 stores the relationship between levels of the measurement signals 81 and type and locations of anomalies; and the anomalous judgment means 80 judges the type and location of an anomaly of a sensor on the basis of levels of the measurement signals 81 and the stored relationship.

According to the tenth aspect of the present invention, the type and location of an anomaly of the sensor can be quickly judged.

According to an eleventh aspect of the present invention, the anomaly detection means 58 detects an anomaly of at least one of the oxygen pump cell 14, the oxygen-partial-pressure detection cell 24, the control circuit 50, and the wiring lines 41, 42, and 43; and the anomaly judgment means 80 judges an anomaly of the sensor on the basis of the levels of the measurement signals 81.

According to the eleventh aspect of the present invention, an anomaly of the vehicle control system can be detected, while a portion(s) of the sensor element, the control circuit, and the wiring lines is specified.

According to a twelfth aspect, the present invention provides a vehicle control system 900, characterized by comprising an oxygen sensor 1 comprising a sensor element 10 including a combination of an oxygen pump cell 14 and an oxygen-partial-pressure detection cell 24; a control circuit 50 connected to the sensor element 10 via wiring lines 41, 42, and 43 and adapted to control the oxygen pump cell 14 such that the output voltage of the oxygen-partial-pressure detection cell 24 is maintained at a predetermined value. The control circuit 50 may also carry out other functions. The oxygen sensor 1 detects the concentration of oxygen contained in a gas to be measured having an oxygen concentration within a predetermined range. The vehicle control system 900 further comprises: storage means 90 for storing the relationship between types and locations of anomalies and the levels of measurement signals 81 of a plurality of types, including a signal 81b corresponding to a magnitude of current flowing through the oxygen pump cell 14, a signal 81c corresponding to an electric potential of the oxygen-partial-pressure detection cell 24, and a signal 81a corresponding to a resistance of the oxygen-partial-pressure detection cell 24; and anomaly judgment means 80 for determining a type and/or location of an anomaly of the sensor, on the basis of levels of the measurement signals 81 and the stored relationship, when the air fuel ratio of an engine is controlled to a lean side and a signal 81c corresponding to an electric potential of the oxygen-partial-pressure detection cell 24 is equal to or lower than a predetermined voltage.

According to the twelfth aspect of the present invention, since an anomaly of the sensor element, the control circuit, or the wiring lines is detected when the air fuel ratio of the engine is on the lean side, a portion which constitutes the oxygen pump cell can be judged to be anomalous when the current flowing through the oxygen pump cell does not reach a theoretical or designed level to be attained.

According to a thirteenth aspect, the present invention provides a vehicle control system 900, wherein the location and/or state of an anomaly of the vehicle control system is determined on the basis of the output level of the signal 81a corresponding to the resistance of the oxygen-partial-pressure detection cell 24.

According to the thirteenth aspect of the present invention, breakage of a wiring line at a portion which constitutes the oxygen-partial-pressure detection cell can be detected on the basis of the output level of the signal 81a corresponding to the resistance of the oxygen-partial-pressure detection cell 24.

According to a fourteenth aspect, the present invention provides a vehicle control system 900, wherein the operation of performing anomaly judgment when the air fuel ratio of the engine is controlled to the lean side is an operation which causes the anomaly judgment means 80 to perform anomaly judgment on the basis of the levels of the measurement signals 81 when the oxygen sensor 1 is exposed to an ambient atmosphere.

According to the fourteenth aspect of the present invention, the anomaly judgment means 80 can clearly judge, on the basis of the levels of the signals 81, whether or not a portion constituting the oxygen pump cell is anomalous, because when the oxygen sensor is exposed to an ambient atmosphere (oxygen concentration: about 20.9%), the magnitude of current flowing through the oxygen pump cell is theoretically at a maximum and is constant.

BRIEF DESCRIPTION OF THE DRAWINGS

FIG. 3 is a table showing electric potential levels at the terminals of the oxygen concentration detection system of FIG. 2 and types of judgment thereof in lean and non-lean regions.

FIG. 7 is a table showing the relationship between signals input to the circuit shown in FIG. 6 and signals output from the circuit.

DESCRIPTION OF REFERENCE NUMERALS

Figure 1:
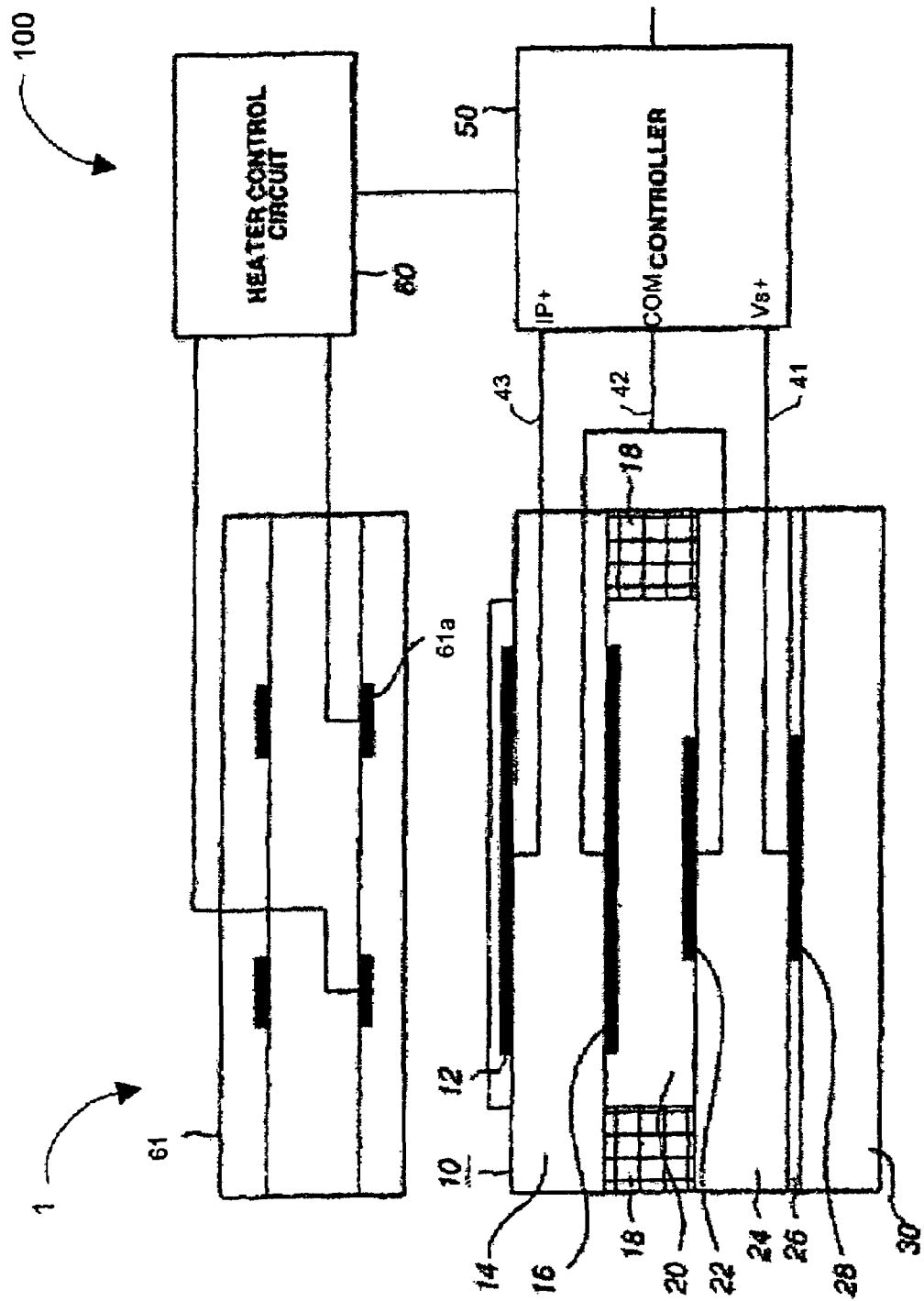
FIG. 1 is a schematic diagram illustrating an oxygen concentration detection system 100 having an oxygen sensor with a heater and control circuits therefor, incorporating anomaly detection means according to the invention.

1: oxygen sensor
8: ECU (engine control unit) having an oxygen concentration detection system
10: sensor element
12, 16, 22, 28: porous electrode
14: pump cell
18: porous diffusion layer
20: clearance
24: oxygen-partial-pressure detection cell
26: reference oxygen chamber
41, 42, 43: wiring line
50: sensor control circuit (sensor controller)
58: self diagnostic circuit
58a, 58b: window comparator
58c: comparator
59a: amplifier
83a: first switch
83b: second switch
60: heater control circuit
61: heater
67: Vs-cell-signal anomaly detection means
68: Vs-cell-signal modification means
70: first comparator
71: second comparator
72: NOR circuit
73: amplifier
74: first analog switch
75: second analog switch
76: third analog switch
200: oxygen concentration detection system
210: sensor element
261: heater for sensor element
250: sensor control circuit
260: heater control circuit
258: anomaly detection means
258d: Switching means
283: output means
280: anomaly judgment means
290: Memory means

DESCRIPTION OF THE PREFERRED EMBODIMENTS

In an oxygen concentration detection system according to a preferred mode of the present invention, a plurality of error signals (anomaly detection signals) are output through a plurality of signal lines, through which at least two types of measurement signals, among the above-described plurality of types of measurement signals, are output; and on a side where the plurality of error signals are received, the location and/or state of an anomaly of the oxygen sensor can be determined from a combination of the error signals.

The oxygen concentration detection system according to the present invention is applied to a vehicle control system which includes an engine and an engine controller.

The oxygen concentration detection system according to the preferred mode of the present invention is configured such that for a wiring line connecting the oxygen sensor element and its control circuit, anomalous conditions of at least three types; i.e., battery-side short circuit, ground-side short circuit, and breakage of the wiring line, can be identified.

The oxygen concentration detection system according to the preferred mode of the present invention includes an oxygen sensor constituted by a combination of an oxygen pump cell and an oxygen-partial-pressure detection cell, and is applied to an air-fuel-ratio measurement system 100 wherein the above-described control circuit controls the oxygen pump cell such that the output voltage of the oxygen-partial-pressure detection cell is maintained at a predetermined value.

The oxygen concentration detection system according to the preferred mode of the present invention uses, as a signal for anomaly detection, a signal representing current flowing through the oxygen pump cell.

The oxygen concentration detection system according to the preferred mode of the present invention uses, as a signal for anomaly detection, an internal resistance signal obtained through conversion of the internal resistance of the oxygen-partial-pressure detection cell to a voltage.

In the oxygen concentration detection system according to the preferred mode of the present invention, since a concentration detection cell signal (which the control circuit of the oxygen sensor element outputs through conversion of a voltage between the opposite ends of the oxygen-partial-pressure detection cell) is output to the engine controller, the concentration detection cell signal can be used as a signal output from the control circuit for anomaly detection.

In the oxygen concentration detection system according to the present invention, the oxygen concentration detection system is applied to a vehicle control system which includes an engine and an engine controller, and the engine controller detects an anomalous state of the air-fuel-ratio detection system when the air fuel ratio of the engine is controlled to the lean side.

In general, the above described "analog signal" is a signal which represents a continuous value. However, in the present specification, that term encompasses a digital signal which selectively represents three or more discrete values. Further, the signal may represents a value of an arbitrary form such as a voltage value or current value.

In the preferred mode of the present invention, when a sensor anomaly is not detected, the measurement signals having levels within predetermined respective ranges are through-output with their levels maintained or amplified in accordance with their levels.

An oxygen concentration detection system according to the present invention will now be described with reference to the drawings, for the case where the oxygen concentration detection system is applied to an air-fuel-ratio detection system (an anomalous detection system for the air-fuel-ratio detection system). However, the present invention should not be construed as being limited thereto.

1. Structure of Sensor Element (Air-Fuel-Ratio Sensor Element)

FIG. 1 shows an example sensor element 10 for use in an oxygen concentration detection system 100 according to an embodiment of the present invention. This sensor element 10 is disposed in an exhaust gas system of an internal combustion engine. The sensor element 10 consists of two cells: an oxygen pump cell 14 and an oxygen-partial pressure detection cell 24 joined together, and is connected to a sensor control circuit 50 via three wiring lines 41, 42, and 43. In ordinary operation, the sensor control circuit 50 mainly performs measurement of the concentration of oxygen contained in exhaust gas and measurement of the temperature of the sensor element 10. In addition, the sensor control circuit 50 has a function of detecting an anomaly of the three wiring lines 41, 42, and 43 connected to the two cells of the sensor element 10.

A heater 61 is mounted to the sensor element 10 via a ceramic joining material, and is controlled by means of a heater control circuit 60. An insulating body of the heater 61 is formed of ceramic such as alumina, and heater wiring 61a is disposed in the body in order to heat the sensor element 10. The heater control circuit 60 supplies electric power to the heater 61 such that the temperature of the sensor element 10 controlled by means of the sensor control circuit 50 is maintained at a target value.

The sensor element 10 is constructed by stacking a oxygen pump cell 14, a porous diffusion layer 18, an oxygen-partial-pressure detection cell 24, and a reinforcement plate 30.

The pump cell 14 is formed into a plate-like shape from wholly or partially stabilized zirconia, which is an oxygen-ion conductive solid electrolyte; and porous electrodes 12 and 16 mainly formed of platinum are provided on opposite surfaces thereof. As described below, current flows between the porous electrodes 12 and 16 in accordance with a change in oxygen concentration of an exhaust gas. The porous electrode 12 on the top surface exposed to a gas under measurement (measurement gas) will be called an Ip+ electrode, whereas the porous electrode 16 on the bottom surface will be called an Ip− electrode. The wiring line 43 is connected to the Ip+ electrode, and the wiring line 42 is connected to the Ip− electrode.

The oxygen-partial-pressure detection cell 24 is also formed of wholly or partially stabilized zirconia; and porous electrodes 22 and 28 mainly formed of platinum are provided on opposite surfaces thereof.

A clearance 20 surrounded by the porous diffusion layer 18 is formed between the pump cell 14 and the oxygen-partial-pressure detection cell 24. The clearance 20 communicates with a measurement gas atmosphere via the porous diffusion layer 18. As described below, electromotive force is generated between the porous electrodes 22 and 28 in accordance with a change in oxygen concentration of exhaust gas. The porous electrode 22, disposed on the side toward the clearance 20, will be called a Vs− electrode, whereas the porous electrode 28, disposed on the side toward a reference oxygen chamber 26, will be called a Vs+ electrode. Reference oxygen within the reference oxygen chamber 26 is generated by causing a very small current (ICP current) to flow from the porous electrode 22 to the porous electrode 28 to thereby pump oxygen within the exhaust gas at a constant rate. The wiring line 41 is connected to the Vs+ electrode, and the wiring line 42 is connected to the Vs− electrode. The wiring line 42 is connected to both the Ip− electrode and the Vs− electrode.

Exhaust gas, which is a measurement gas, diffuses into the clearance 20 through the porous diffusion layer 18. When the air fuel ratio of exhaust gas discharged from the engine coincides with the theoretical air fuel ratio, on the basis of the Nernst equation, a potential difference of about 450 mV arises between the Vs+ electrode 28 and the Vs− electrode 22 of the oxygen-partial-pressure detection cell 24 stemming from the difference in oxygen concentration between the clearance 20 and the reference oxygen chamber 26, in which a constant oxygen concentration is maintained. In this manner, the atmosphere within the clearance 20 is controlled such that its oxygen concentration always corresponds to the theoretical air fuel ratio. Specifically, the sensor control circuit 50 adjusts the current Ip flowing through the oxygen pump cell 14 such that the electromotive force Vs of the oxygen-partial-pressure detection cell 24 becomes 450 mV, to thereby pump oxygen. In this state, the current Ip flowing through the pump cell 14 is measured, whereby the air fuel ratio of the measurement gas can be determined.

As described above, by means of the sensor control circuit 50, the current Ip flowing through the oxygen pump cell 14 of the sensor element 10 is adjusted such that the electromotive force Vs of the oxygen-partial-pressure detection cell 24 becomes 450 mV. Therefore, by utilizing the flow characteristics of the Ip current of the sensor element 10 controlled by the sensor control circuit 50, anomaly detection for the wiring lines 41, 42, and 43 of the sensor element 10, as described below, becomes possible.

2. Configuration of the Sensor Control Circuit

Figure 2:
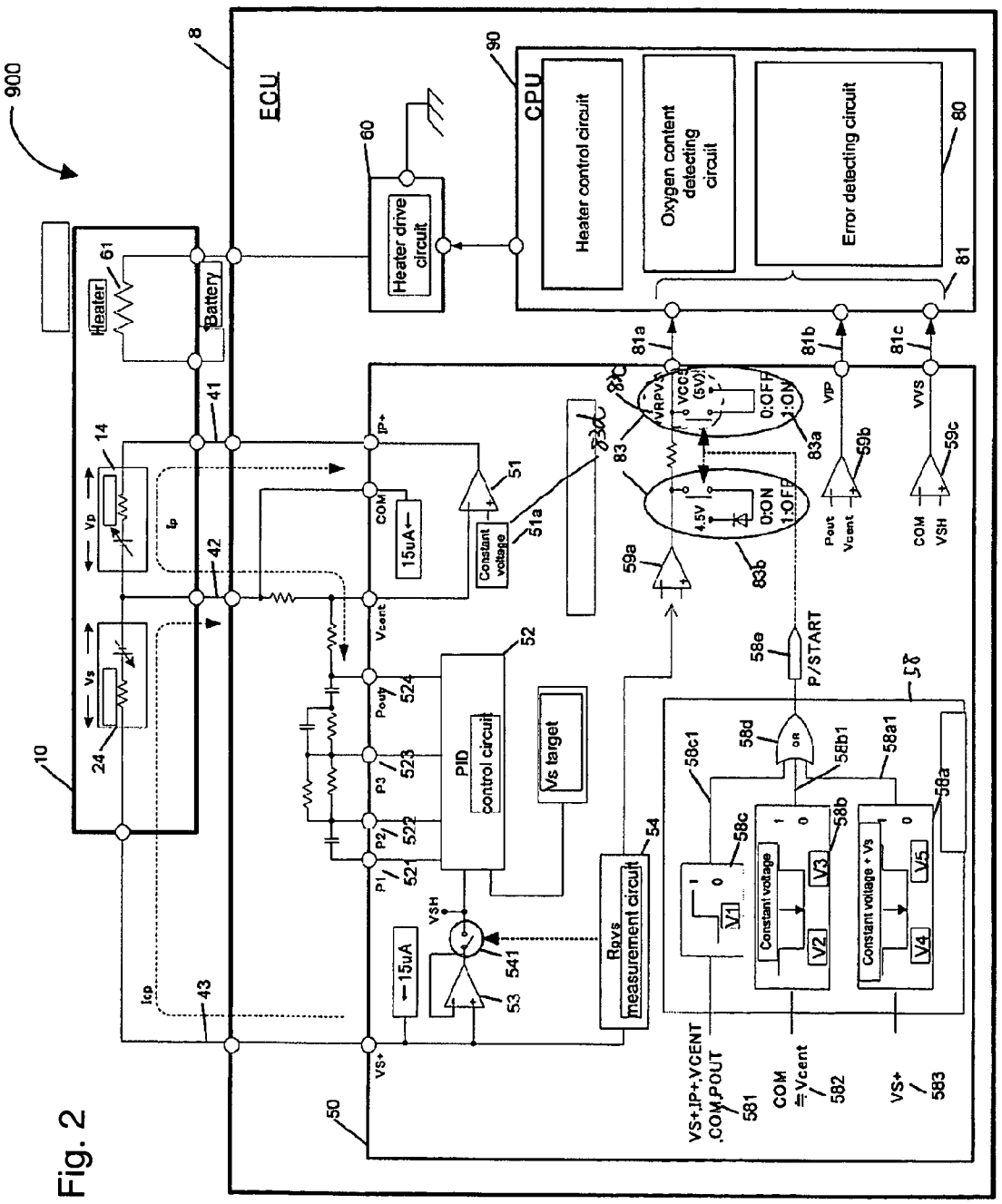
FIG. 2 is a detailed circuit diagram of a vehicle control system 900 comprising the oxygen concentration detection system having an anomaly detection means according to the invention.

Next, the sensor control circuit 50 for controlling the above-described sensor element will be described in detail. FIG. 2 is a diagram illustrating the configuration of the control circuit for the sensor element shown in FIG. 1.

Referring to FIG. 2, the sensor control circuit 50 mainly consists of an Ip driver 51 constituted by an operational amplifier; a PID control circuit 52; an operational amplifier 53; an Rpvs measurement circuit 54 for measurement of an internal resistance of the oxygen-partial pressure detection cell; and a self diagnostic circuit 58. The sensor control circuit 50 may be constituted by use of ordinary electric components and incorporated directly into an engine controller 8. Alternatively, only the sensor control circuit 50 may be integrated into a single integrated circuit; i.e., an ASIC (Application Specific IC).

Output terminals (output means) VIP, VVS, and VRPVS of the sensor control circuit 50 are connected to respective analog input terminals of a processing unit (CPU) 90 provided within an engine control unit (ECU) 8.

The sensor control circuit 50 can be configured to output a P/START signal to the VRPVS terminal (the VIP terminal and the VVS terminal in some cases) as a superposition signal. Specifically, in accordance with the level of the P/START signal whose level changes depending on whether the sensor is normal or anomalous, the output terminals VIP, VVS, and VRPVS output voltages representing measurement values or a voltage indicative of an anomaly of the sensor. More specifically, when the sensor is normal, a voltage in proportion to the magnitude of the later described Rpvs is through-output from the VRPVS terminal. When the sensor is normal, a voltage in proportion to the magnitude of current flowing between the Ip+ and Ip− electrodes of the oxygen pump cell 14 is through-output from the VIP terminal, and a voltage in proportion to the voltage difference between the Vs+ and Vs− electrodes of the oxygen-partial pressure detection cell 24 is through-output from the VVS terminal. Meanwhile, when the sensor is anomalous, a predetermined voltage is selectively output from a predetermined terminal, through modification of the level of the corresponding signal to a level that the signal does not assume in an ordinary state.

The Ip driver 51 is an operational amplifier for supplying Ip current to the sensor element 10. A Vcent terminal is connected to the inverted input terminal of the operational amplifier, and a reference voltage (3.6 V in the present embodiment) is supplied to the non-inverted input terminal of the operational amplifier. An IP+ terminal is connected to the output terminal of the operational amplifier. The oxygen pump cell 14 of the sensor element 10 is connected between the Vcent terminal and the IP+ terminal. Since the Ip driver 51 forms a negative feedback circuit, the Ip current is controlled such that the electric potential at the Vcent terminal is always maintained at the reference voltage (3.6 V). The Ip driver 51 cooperates with the PID control circuit 52 so as to maintain the voltage of the Vcent terminal at 3.6 V (reference voltage), whereby the pump current (Ip current) is controlled such that the electromotive force Vs coincides with a control target.

The PID control circuit 52 constitutes a PID calculation circuit in cooperation with resistors and capacitors connected to a P1 terminal 521, a P2 terminal 522, and a P3 terminal 523, which are input/output terminals. The PID control circuit 52 performs PID calculation for a deviation ΔVs of the electromotive force Vs of the oxygen-partial-pressure detection cell 24 with respect to the Vs control target (450 mV), and outputs a resultant voltage to a Pout terminal 524.

Specifically, when the electromotive force Vs of the oxygen-partial-pressure detection cell 24 is higher than 450 mV, the oxygen concentration in the clearance 20 is lower than that in a theoretical air fuel ratio; i.e., the air fuel ratio of the measurement gas is on the rich side, where fuel supply is excessive, with respect to the theoretical air fuel ratio. In this case, the voltage obtained from the deviation ΔVs through PID calculation and output from the Pout terminal 524 changes so as to induce an Ip current for causing the pump cell 14 to pump in oxygen so as to eliminate a shortfall of oxygen. Meanwhile, when the electromotive force Vs of the oxygen-partial-pressure detection cell 24 is lower than 450 mV, the oxygen concentration in the clearance 20 is higher than that in the theoretical air fuel ratio; i.e., the air fuel ratio of the measurement gas is on the lean side, where fuel supply is insufficient, with respect to the theoretical air fuel ratio. In this case, the voltage obtained from the deviation ΔVs through PID calculation and output from the Pout terminal 524 changes so as to induce an Ip current for causing the pump cell 14 to pump out excessive oxygen.

Notably, a constant current source of −15 μA is connected to a COM terminal, to which the wiring line 42 is connected, in order to eliminate error in an Ip output signal. Specifically, a constant current source of +15 μA is connected to a VS+ terminal in order to supply Icp current to the oxygen-partial-pressure detection cell 24, to thereby create an oxygen reference. Therefore, the constant current source of −15 μA is connected to the COM terminal in order to subtract 15 μA from the current flowing into the PID control circuit 52, to thereby eliminate calculation error stemming from the Icp current.

The operational amplifier 53 connected between the VS+ terminal and the PID control circuit 52 forms a voltage follower circuit. As a result, the PID control circuit 52 has a high impedance as viewed from the VS+ terminal, whereby the current supplied from the +15 μA constant current source is prevented from flowing into the PID control circuit 52.

The Rpvs measurement circuit 54 is adapted to measure the temperature of the sensor element 10 on the basis of the internal resistance Rpvs of the oxygen-partial-pressure detection cell 24, and is constituted by an operational amplifier, resistors, capacitors, etc. The Rpvs measurement circuit 54 supplies a predetermined measurement current to the oxygen-partial-pressure detection cell 24 at predetermined intervals, to thereby cause a voltage change which corresponds to the internal resistance of the oxygen-partial-pressure detection cell 24, which resistance has a correlation with the element temperature. The thus-obtained change in the voltage between the opposite ends of the oxygen-partial-pressure detection cell 24 is multiplied by a constant to thereby obtain a VRpvs voltage (within a range of 0 to 4.5V in the present embodiment).

When the Rpvs measurement circuit 54 supplies measurement current to the oxygen-partial-pressure detection cell 24, the connection between the PID control circuit 52 and the operational amplifier 53 is broken by means of a switch 541 provided therebetween, to thereby prevent the voltage change stemming from the measurement current from causing a change in the output of the PID control circuit 52. During periods in which the connection between the PID control circuit 52 and the operational amplifier 53 is broken by the switch 541, the Rpvs measurement circuit 54 measures the internal resistance of the oxygen-partial-pressure detection cell 24; i.e., the temperature of the sensor element.

Next, the self diagnostic circuit 58 for detection sensor anomaly and terminals for outputting signals indicative of sensor anomaly will be described. Notably, examples of sensor anomaly include wire breakage, a short circuit between the wiring and a battery power line, and failure of the sensor element.

The self diagnostic circuit (anomaly detection means and modification means) 58 includes window comparators 58a and 58b, a comparator 58c, an OR circuit 58d, and an amplifier 59a. The self diagnostic circuit 58 can detect anomaly of, for example, the sensor element 10, and the three wiring lines 41, 42, and 43 connected to the two cells of the sensor element 10. When the self diagnostic circuit 58 detects a sensor anomaly, the self diagnostic circuit 58 outputs a P/START signal 58e whose level differs from the level in the ordinary state. As a result, a signal indicative of a sensor anomaly is output from the VRPVS terminal, which outputs a VRPVS signal.

The window comparator 58a, which is one of the anomaly detection means, judges whether or not the electric potential at the VS+ terminal falls within a predetermined range. In an ordinary state, the electric potential at the VS+ terminal is maintained at a value (4.05 V, in the present embodiment) which corresponds to the sum of the reference voltage (3.6 V) at the COM terminal and the electromotive force Vs (450 mV) of the oxygen-partial-pressure detection cell 24. The upper limit and lower limit of the window comparator 58a are set on the basis of the sum of the reference voltage and the electric potential in the ordinary state. Therefore, when the electric potential at the VS+ terminal exceeds the upper limit (6.35 V in the present embodiment) or falls below the lower limit (2.5 V in the present embodiment), an anomaly is judged to have occurred, and a signal of a predetermined level is output from the window comparator 58a.

The window comparator 58b, which is one of the anomaly detection means, judges whether the electric potential at the COM terminal falls within a predetermined range. The electric potential at the COM terminal is controlled by the Ip driver 51 to coincide with the reference voltage (3.6 V) at all times. The upper limit and lower limit of the window comparator 58b are set on the basis of the electric potential in the ordinary state. Therefore, when the electric potential at the COM terminal exceeds the upper limit (5.5 V in the present embodiment) or falls below the lower limit (2.5 V in the present embodiment), an anomaly is judged to have occurred, and a signal of a predetermined level is output from the window comparator 58b.

The comparator 58c, which is one of the anomaly detection means, judges whether the electric potential at any of the VS+ terminal, the IP+ terminal, the Vcent terminal, the COM terminal, and the Pout terminal of the sensor control circuit 50 exceeds the drive voltage (8 V in the present embodiment) of the sensor control circuit 50. These terminals are monitored by the comparator 58c, the upper limit of which is set in consideration of voltage variation of the drive power source and other relevant factors. When the electric potential at one of these terminals exceeds the upper limit, the terminal is judged to have been short-circuited to the battery power line BATT, resulting in occurrence of anomaly, and a signal of a predetermined level is output from the comparator 58c.

The output signals of these three comparators 58a, 58b, and 58c are fed to the OR circuit 58d, and the logical OR result of these output signals is output from the OR circuit 58d as the P/START signal 58e. Therefore, the P/START signal 58e assumes different levels depending on whether the sensor is normal or anomalous. For example, the P/START signal 58e assumes a "O" level when the sensor is normal, and a "1" level when the sensor is anomalous. The P/START signal 58e is supplied to a first switch 83a and a second switch 83b as a control signal, in order to turn on and off these switches as shown in FIG. 2 in accordance with the level of the P/START signal 58e.

The input terminal of the amplifier 59a is connected to the output terminal of the Rpvs measurement circuit 54, and the VRPVS terminal is connected to the output terminal of the amplifier 59a. Through switching of the first and second switches 83a and 83b, when the sensor is normal, the second switch 83b is maintained on and the first switch 83a is maintained off, whereby the electric potential at the output terminal of the amplifier 59a appears at the VRPVS terminal as is; i.e., a voltage within a predetermined range (a range of 0 to 4.5 V in the present embodiment) is through-output from the VRPVS terminal (may be output after being amplified). In contrast, when the sensor becomes anomalous, the second switch 83b is turned off and the first switch 83a is turned on, whereby an electric potential of VCC5 appears at the VRPVS terminal; i.e., a predetermined voltage (5 V in the present embodiment) is output from the VRPVS terminal, through modification of the level of the signal to a level which the signal does not assume when the sensor is normal.

Next, examples of levels of signals which are output from the VRPVS terminal, the VIP terminal, and the VVS terminal at the time of sensor anomaly will be described. Referring to FIG. 2, when one of the three comparators 58a, 58b, and 58c detects sensor anomaly, the level of the P/START signal 58e changes from Low level (0) to High level (1), whereby the first switch 83a is turned on. As a result, the VCC5 is connected to the VRPVS terminal, whereby the electric potential at the VRPVS terminal is forcedly changed to a predetermined level (5 V in the present embodiment) which the signal does not assume when the sensor is normal. At this time, the CPU 90 having an analog port connected to the VRPVS terminal detects that the VRPVS terminal has an electrical potential (5 V in the present embodiment) which the signal does not assume when the sensor is normal, and thus judges that an anomaly has occurred in the sensor. Notably, the VIP terminal and the VVS terminal, connected to the outputs of amplifiers 59b and 59c, respectively, each outputs a voltage which varies depending on the status of the sensor anomaly.

Anomaly detection is preferably executed when the air fuel ratio is controlled to the lean side, in particular when exhaust gas is equivalent to the ambient atmosphere. When the air fuel ratio is on the rich side, Ip and Vs may vary greatly in some cases. Further, the ECU 8 including the CPU 90 can make final determination whether or not the sensor is anomalous.

3. Advantages of the Present Embodiment

As described above, in the present embodiment, when the sensor is anomalous, a signal having a level that is indicative of sensor anomaly is output from the VRPVS terminal. This eliminates the necessity of providing an additional signal line for transmitting a signal indicative of sensor anomaly. Accordingly, an increase in the degree of complication of routing of signal lines, stemming from provision of additional signal lines, is prevented, and the risk of breakage of wiring lines is lowered.

In the above-described embodiment of the present invention, a signal indicative of sensor anomaly is output from the VRPVS terminal. However, such a signal may be output from other terminals. Moreover, in the above-described embodiment of the present invention, upon detection of sensor anomaly, a single type of signal is output from the VRPVS terminal. However, a signal whose level changes depending on the location and/or status of sensor anomaly may be output from the VRPVS terminal, from the VRPVS terminal and other terminals, or from other terminals.

4. Other Embodiments

Another embodiment of the present invention will next be described. FIGS. 3 to 7 are diagrams illustrating an example in which the manner of outputting signals is changed in accordance with the type of and location of sensor anomaly by use of the oxygen concentration detection system shown in FIG. 2.

Figure 4:
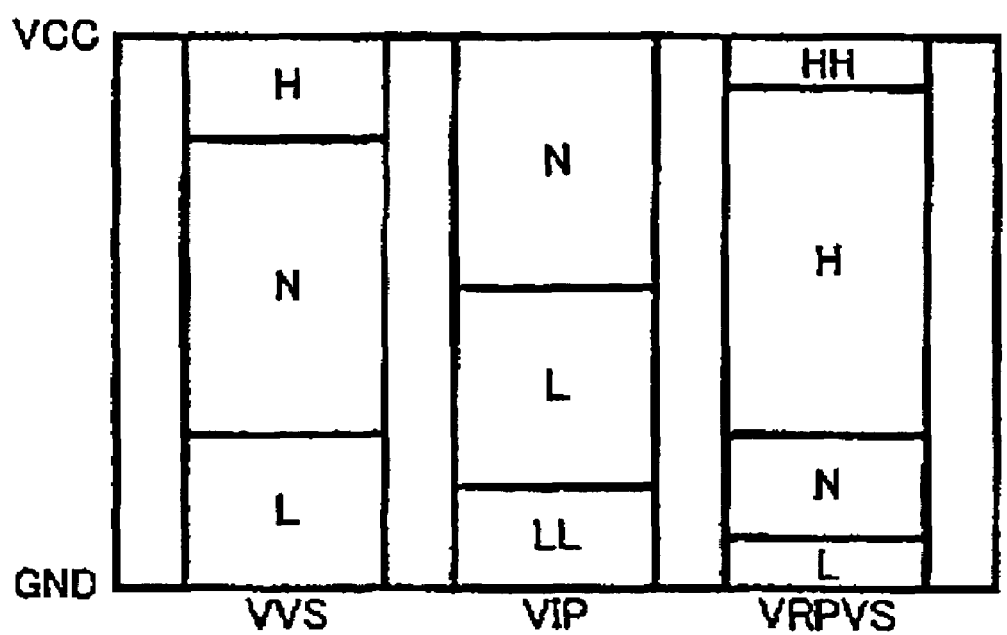
FIG. 4 is a diagram which illustrates ranges of electric potentials at the terminals of FIG. 2.

Referring to FIGS. 3 and 4, when one of the VS+ terminal, the IP+ terminal, and the COM terminal short-circuits to the battery power line, the electric potentials of the VVS terminal and the VIP terminal are set to a potential lower than that of the normal state, and the electric potential of the VRPVS terminal is set to a potential higher than that of the normal state. Similarly, when one of the VS+ terminal, the IP+ terminal, and the COM terminal short-circuits to the ground, the electrical potentials of these terminals are set as shown in FIGS. 3 and 4.

When the air fuel ratio is in a fuel-rich region, the voltage at the VIP terminal is lower than a normal value. This is due to voltage reduction at the VIP terminal (so as to be lower than the range as set in FIG. 4) by the oxygen pump cell 14 that pumps oxygen from outside to inside when the air fuel ratio is shifted to the rich region. This means that when the air fuel ratio is not in a fuel-lean region, the mode of the anomaly judgment is limited.

On the other hand, when the air fuel ratio is on the lean side or when exhaust gas is substantially equivalent to the ambient atmosphere, the VVS lead terminal and VRPVS lead terminal show normal electric potentials while the VIP lead terminal shows a lower voltage (the L value in FIG. 4). This combination indicates the state of wire breakage, judging that the IP+ lead terminal is open.

A vehicle control system 900 according to the invention, has an anomaly detection system (or rather error detection means or failure detection means) in which, data regarding the threshold-judgment information based on VVS voltage, VIP voltage, and VRPVS voltage are previously stored, for instance, in a CPU 90. The signals outputted from a self diagnostic circuit 58 through an output means 83 are inputted into the CPU 90, and they are compared with the threshold-judgment information so as to detect anomalous conditions or locations such as a battery-side short circuit, a ground-side short circuit, and breakage of wiring lines, anomaly of the sensor element, anomaly of the control circuit including the VS+ terminal, the IP+ terminal and COM terminal. Since occurrence of the above anomaly can be clearly determined from these respective voltages, the oxygen concentration detection system 100 and the vehicle control system 900 incorporating the anomaly detection means 58 according to the invention, can detect a failure or anomaly mode as it occurs.

Moreover, as described below, since the combination of electric potentials of the VVS terminal, the VIP terminal, and the VRPVS terminal can be changed freely in accordance with the type of anomaly, the ECU, which receives the outputs, can identify the specifics of the anomaly by interpreting the combination, without the necessity of increasing the number of signal lines.

Figure 5:
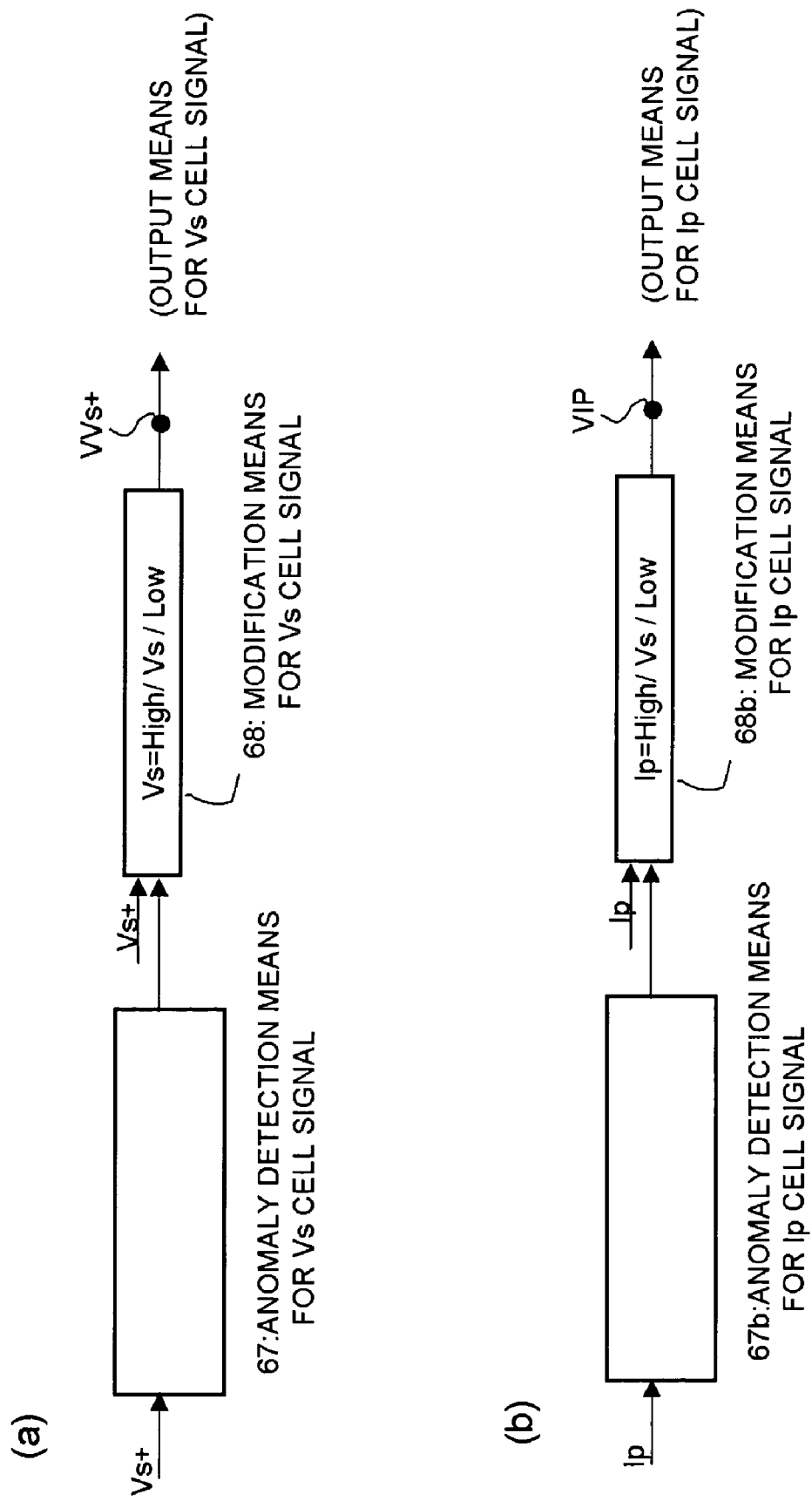
FIG. 5 is a diagram of a circuit for selectively outputting three output signals (High, Normal, Low), which are applied to the control circuit of FIG. 2.

The configuration of the above-described anomaly detection means 58, etc., for generating various signals in accordance with the type of anomaly will next be described. FIG. 5(*a*) is a diagram showing the configurations of Vs-cell-signal anomaly detection means 67 and Vs-cell-signal modification means 68 to which output means for Vs cell signal (corresponding 81*c* of FIG. 2) is connected. FIG. 5(*b*) is a diagram showing the configuration of Ip-cell signal anomaly detection means 67*b* and Ip-cell signal modification means 68*b* to which output means for Ip-cell signal (corresponding to 81*b* of FIG. 2) is connected.

Referring to FIG. 5(*a*), the voltage of the VS+ terminal is fed to Vs-cell-signal anomaly detection means 67, which outputs different control signals for the case where the VS+ terminal voltage falls within a normal range, the case where the VS+ terminal voltage falls below a predetermined range, and the case where the VS+ terminal voltage is above the predetermined range. Similarly, Referring to FIG. 5(*b*), the voltage of the Ip terminal is fed to IP cell-signal anomaly detection means 68*b*, which outputs different control signals for the case where the VIP terminal voltage falls within a normal range, the case where the VIP terminal voltage falls below a predetermined range, and the case where the VIP terminal voltage is above the predetermined range.

In accordance with the control signals output from the Vs-cell-signal anomaly detection means 67, Vs-cell-signal modification means 68 outputs from the VVS+ terminal (to Vs-cell-signal output means 81 of FIG. 2) a voltage corresponding to the VS+ terminal voltage (through-output, however, the signal may first be amplified) when the VS+ terminal voltage falls within the normal range, a voltage corresponding to Low of FIG. 4 when the VS+ terminal voltage falls below the predetermined range, and a voltage corresponding to High of FIG. 4 when the VS+ terminal voltage is above the predetermined range. In accordance with the control signals output from the Ip-cell-signal anomaly detection means 67*b*, function and operation similar to those explained above occurs through the Ip-cell-signal modification means 68*b*.

Figure 6:
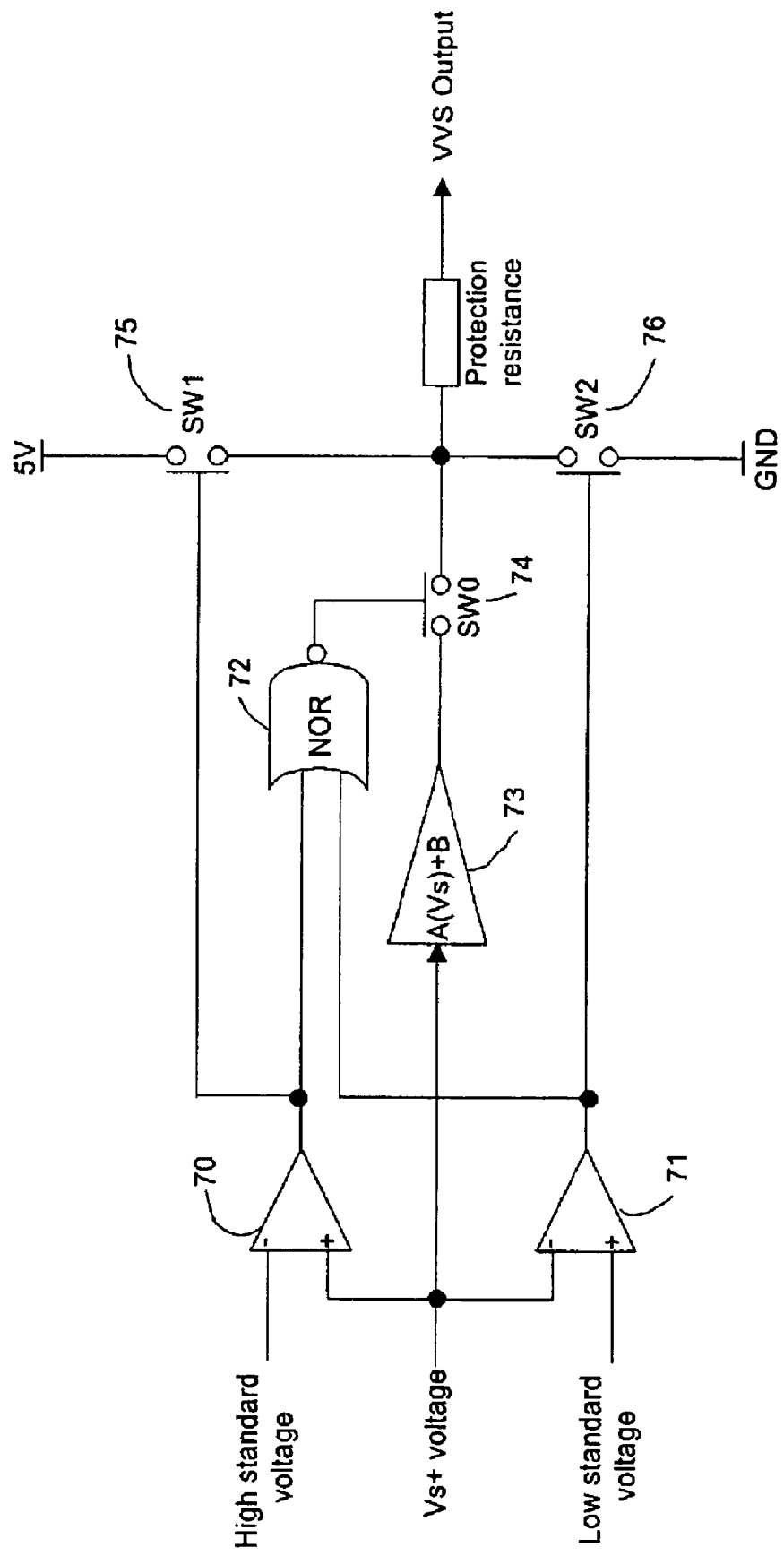
FIG. 6 is a diagram illustrating another circuit configuration of an anomaly detection means and modification (or switching) means, which may be used in the oxygen concentration detection system of FIG. 2.

Next, the circuit for selectively outputting three output signals (High, Normal, Low) shown in FIG. 5 will be described. FIG. 6 is a diagram for explaining the circuit for selectively outputting three output signals (High, Normal, Low), which is applied to the control circuit shown in FIG. 2. FIG. 7 is a table showing the relationship between signals input to the circuit shown in FIG. 6 and signal output from the circuit.

Referring to FIG. 6, the Vs-cell-signal anomaly detection means 67 includes a first comparator 70, a second comparator 71, and a NOR circuit 72. The Vs-cell-signal modification means 68 includes a first analog switch 74, a second analog switch 75, and a third analog switch 76.

Operation of the circuit shown in FIG. 6 will now be described with reference to FIG. 7. The first comparator 70 outputs High when the Vs+ voltage falls within an anomalous range above the normal range. The second comparator 71 outputs High when the Vs+ voltage falls within an anomalous range below the normal range.

When the Vs+ voltage (Vs+ signal) falls within the normal range, Low is output from the first comparator 70 and the second comparator 71, whereby High is output from the NOR circuit 72. As a result, only the first analog switch 74 is turned on, and thus the Vs+ voltage amplified by an amplifier 73 is output from a predetermined terminal (output means) as is. When the Vs+ voltage (Vs+ signal) falls within the anomalous range above the normal range, High is output from the first comparator 70, and Low is output from the second comparator 71, whereby only the second analog switch 75 is turned on, and a predetermined voltage (5 V in the present embodiment) is output from the predetermined terminal (output means) as is.

When the Vs+ voltage (Vs+ signal) falls within the anomalous range below the normal range, Low is output from the first comparator 70, and High is output from the second comparator 71, whereby only the third analog switch 76 is turned on, and 0 V voltage is output from the predetermined terminal (output means) as is.

The circuit of FIG. 6 for processing the VS signal may be used as a circuit for processing other signals.

Notably, the present invention is not limited to the above-described embodiments, and the above-described embodiments may be modified in various manners, within the scope of the invention, in accordance with purposes and applications. For example, the anomaly to be detected is not limited to those in which the electric potential at each terminal exceeds a predetermined range, and an anomaly can be detected on the basis of other conditions, such as when two terminals assume the same potential because of inter-line short circuit, or other causes.

In the above-described embodiments, a full range air-fuel-ratio sensor including two cells formed of oxygen-ion conductive solid electrolyte is used as a sensor for air fuel ratio detection. However, an oxygen sensor including a single cell may be used.

According to the present invention, an error signal for reporting the occurrence of an anomaly in an oxygen sensor is transmitted a signal line which is generally used for transmitting various measurement signals output from the oxygen sensor. Therefore, provision of an additional signal line is not required for reporting the occurrence of an anomaly of the oxygen sensor, and thus the number of signal lines can be reduced.

Figure 8:
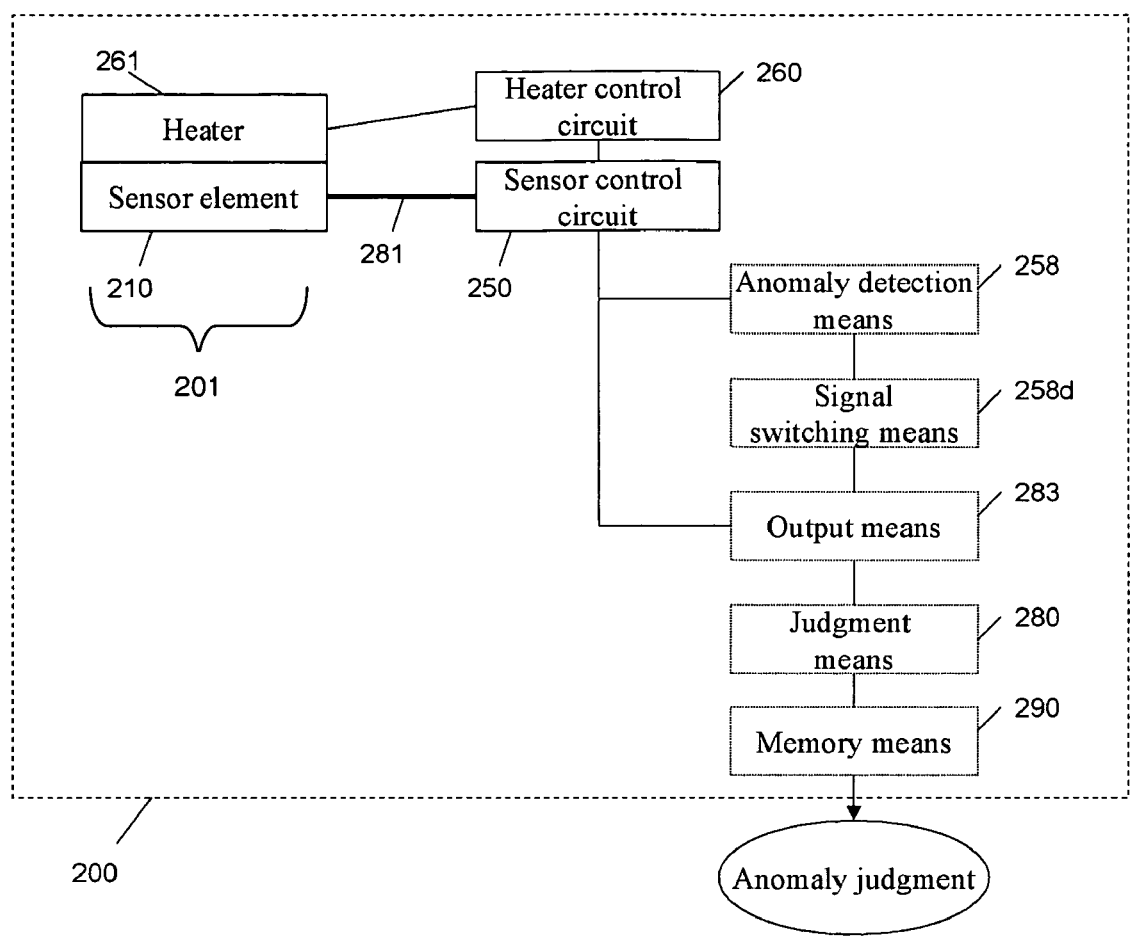
FIG. 8 is a general diagram illustrating a flow for anomaly judgment in the oxygen concentration detection system according to the invention.

According to the invention, as is outlined in FIG. 8, the oxygen concentration detection system 200 and the vehicle control system having the same comprises an oxygen sensor 201 having a sensor element 210 with a heater 261 for heating the sensor element 210; a sensor control circuit 250 for controlling the oxygen sensor 201; a anomaly detection means 258 for detecting anomaly of the oxygen sensor 201 based on that at least one of electric potentials at the sensor and/or control circuits 250, 260 is outside a predetermined respective electric potential range; a modification or switching means 258*d* for issuing a first instruction when the anomaly detection means 258 does not detect any anomaly, the first instruction showing non-detection of anomaly, and for issuing a second instruction when the anomaly detection means 258 detects a sensor anomaly, the second instruction corresponding to the detected anomaly; and output means 283 for through-outputting the measurement signal 281 when the modification or switching means 258d outputs the first instruction signal and for outputting at least a selected one of the measurement signals 281 when the modification or switching means 258d outputs the second instruction signals, the selected measurement signal 281 being modified or switched so as to report a level outside the corresponding range within which the level of the selected measurement signal 281 varies in a normal state. An important feature of the oxygen concentration detection system 200 is that an anomaly detection through anomaly detection means 280 is performed based on at least one (preferably plurality) of signals including measurement signals 281 sent from the sensor 201 and/or those from the control circuits 250,260, and then anomaly is reported by a voltage modified by the signal switching means 258d (or rather signal modification means) through output means 283 to anomaly means 280, said voltage thus modified being outside (not within) a respective normal range of the measurement signals 281. By adopting the signal modification (or rather signal switching means) 258d, no additional signal line or terminal is necessary in the sensor 201 and/or the control circuits 250,260 for anomaly detection.

Preferably, the oxygen concentration detection system 200 comprises judgment means 280 for judging anomaly (or rather failure or error) of the oxygen concentration detection system 200 based on the plurality of signals including measurement signals 281 of the oxygen sensor 201.

The anomaly judgment is conducted under consultation with memory means 280 in which data is stored. The data stored in the memory means 290 are specific conditions based on which, kinds of anomaly (or malfunction) and locations where anomaly has occurred in the oxygen concentration detection system 200 can be determined. An accurate judgment is attained when the oxygen concentration detection system 200 incorporating such anomaly detection means performs anomaly judgment based on combination of levels of the measurement signals 281, which are compared with the data predetermined and stored in the memory means 290 in which threshold levels and their corresponding judgment as referred in the table of FIG. 3 is preliminarily memorized.

This application is based on Japanese Patent Application No. 2003-74362, filed Mar. 18, 2003, incorporated herein by reference in its entirety.

What is claimed is:

1. An oxygen concentration detection system having an oxygen sensor comprising a sensor element including a combination of an oxygen pump cell and an oxygen-partial-pressure detection cell; a control circuit connected to the sensor element via wiring lines adapted to control the oxygen pump cell such that the output voltage of the oxygen-partial-pressure detection cell is maintained at a predetermined value, the oxygen sensor detecting the concentration of oxygen contained in a gas to be measured having an oxygen concentration within a predetermined range, and the oxygen concentration detection system outputting measurement signals of a plurality of types, including a first signal corresponding to a magnitude of current flowing through the oxygen pump cell, a second signal corresponding to an electric potential of the oxygen-partial-pressure detection cell, and a third signal corresponding to a resistance of the oxygen-partial-pressure detection cell, the oxygen concentration detection system comprising:

anomaly detection means for detecting a sensor anomaly by determining whether at least one of respective levels of signals which represent electric potentials at different portions of the sensor element, the wiring lines, and the control circuit falls within a predetermined range;

modification means for issuing a first instruction when the anomaly detection means does not detect an anomaly, the first instruction indicating non-detection of an anomaly, and for issuing a second instruction when the anomaly detection means detects a sensor anomaly, the second instruction corresponding to the detected anomaly; and output means for through-outputting the measurement signals when the modification means outputs the first instruction signal and for outputting a selected measurement signal modified to have a level outside the corresponding range within which the level of the selected measurement signal varies in a normal state.

2. The oxygen concentration detection system as claimed in claim 1, wherein the anomaly detection means detects an anomaly of at least one of the oxygen pump cell, the oxygen-partial-pressure detection cell, the control circuit, and the wiring lines.

3. The oxygen concentration detection system as claimed in claim 1, wherein both a measurement signal in a normal state and measurement signal modified to have a level falling outside the predetermined range are output through the same signal line.

4. The oxygen concentration detection system as claimed in claim 1, wherein the output means includes (i) switches for switching their connection states in accordance with an instruction from the modification means and (ii) a constant voltage power source, wherein when the second instruction indicative of an anomaly is output from the modification means, the constant voltage power source is connected, through a switching operation of the switches, to a signal line to which a selected one of the measurement signals is output, to thereby change the level of the selected measurement signal to a level falling outside the predetermined range within which the level of the measurement signal varies in a normal state.

5. The oxygen concentration detection system as claimed in claim 1, wherein when a sensor anomaly occurs, the anomaly detection means determines that the level of one of the signals which represent electric potentials at different portions of the sensor element, the wiring lines, and the control circuit falls outside the corresponding predetermined range, and outputs a predetermined anomaly detection signal in accordance with the type and level of the signal whose level falls outside the predetermined range;

the modification means issues, in accordance with the anomaly detection signal output from the anomaly detection means, a control signal for specifying a signal which is to be output at a level falling outside the corresponding range within which the level of the signal varies in a normal state; and the output means outputs, on the basis of the control signal output from the modification means, at least one of the measurement signals specified by the modification means, at a predetermined level falling outside the corresponding range within which the level of the signal varies in a normal state, whereby the location and/or state of the anomaly of the sensor element is reported.

6. The oxygen concentration detection system as claimed in claim 1, wherein the anomaly detection means, the modification means, and the output means are provided in the control circuit of the sensor element.

7. The oxygen concentration detection system as claimed in claim 1, wherein the oxygen sensor includes a heater for heating the sensor element; and a heater control circuit for controlling electric power supplied to the heater such that the sensor element is maintained at a predetermined temperature.

8. The oxygen concentration detection system as claimed in claim 1, wherein when an anomaly is detected in the signals representing the electric potentials at the different locations, the output means changes the level of a measurement signal corresponding to the resistance of the oxygen-partial-pressure detection cell to a level falling outside the predetermined range in which the level of the measurement signal varies in a normal state.

9. A vehicle control system comprising:
an oxygen sensor comprising a sensor element including a combination of an oxygen pump cell and an oxygen-partial-pressure detection cell; a control circuit connected to the sensor element via wiring lines and adapted to control the oxygen pump cell such that the output voltage of the oxygen-partial-pressure detection cell is maintained at a predetermined value, the oxygen sensor detecting concentration of oxygen contained in a gas to be measured having an oxygen concentration within a predetermined range;
anomaly detection means for detecting a sensor anomaly by determining whether or not at least one of respective levels of signals which represent electric potentials at different portions of the sensor element, the wiring lines, and the control circuit falls within a predetermined range;
modification means for issuing a first instruction when the anomaly detection means does not detect an anomaly, the first instruction indicating non-detection of an anomaly, and for issuing a second instruction when the anomaly detection means detects a sensor anomaly, the second instruction corresponding to the detected anomaly;
output means for through-outputting the measurement signals when the modification means outputs the first instruction signal and for outputting at least a selected one of the measurement signals when the modification means outputs the second instruction signal, the selected measurement signal being modified to have a level outside the corresponding range within which the level of the selected measurement signal varies in a normal state; and
anomaly judgment means for judging whether or not the vehicl anomalous, on the basis of measurement signals of a plurality of types, including a first signal corresponding to a magnitude of current flowing through the oxygen pump cell, a second signal corresponding to an electric potential of the oxygen-partial-pressure detection ccli, and a third signal corresponding to a resistance of the oxygen-partial-pressure detection cell.

10. The vehicle control system as claimed in claim 9, wherein the anomalous judgment means stores a relationship between levels of the measurement signals and type and locations of anomalies; and the anomalous judgment means determines the type and location of an anomaly of a sensor on the basis of levels of the measurement signals and the stored relationship.

11. The vehicle control system as claimed in claim 9, wherein the anomaly detection means detects an anomaly of at least one of the oxygen pump cell, the oxygen-partial-pressure detection cell, the control circuit, and the wiring lines; and the anomaly judgment means judges an anomaly of the sensor on the basis of the levels of the measurement signals.

12. A vehicle control system, comprising:
an oxygen sensor comprising a sensor element including a combination of an oxygen pump cell and an oxygen-partial-pressure detection cell; a control circuit connected to the sensor element via wiring lines and adapted to control the oxygen pump cell such that the output voltage of the oxygen-partial-pressure detection cell is maintained at a predetermined value, the oxygen sensor detecting the concentration of oxygen contained in a gas to be measured having an oxygen concentration within a predetermined range;
storage means for storing a relationship between types and locations of anomalies and levels of measurement signals of a plurality of types, including a first signal corresponding to a magnitude of current flowing through the oxygen pump cell, a second signal corresponding to an electric potential of the oxygen-partial-pressure detection cell, and a third signal corresponding to a resistance of the oxygen-partial-pressure detection cell; and
anomaly judgment means for specifying a type and/or location of an anomaly in the wiring lines, based on comparing levels of at least said three measurement signals and the stored relationship, when the air fuel ratio of an engine is controlled to a fuel-lean region and the second signal corresponding to the electric potential of the oxygen-partial-pressure detection cell is equal to or lower than a predetermined voltage.

13. A vehicle control system as claimed in claim 12, wherein the operation of performing an anomaly judgment when the air fuel ratio of the engine is controlled to the fuel-lean region causes the anomaly judgment means to perform an anomaly judgment on the basis of the levels of at least said three measurement signals when the oxygen sensor is exposed to ambient atmosphere.

14. An oxygen concentration detection system, comprising an oxygen sensor having a sensor element with a heater for heating the sensor element; a sensor control circuit for controlling the sensor; an anomaly detection means for detecting an anomaly of the sensor when at least one of measurement signals at the sensor control circuit has an electric potential falling outside a predetermined range; a modification or switching means for issuing a first instruction when the anomaly detection means does not detect an anomaly, the first instruction indicating non-detection of an anomaly, and for issuing a second instruction when the anomaly detection means detects a sensor anomaly, the second instruction corresponding to the detected anomaly; and output means for through-outputting a corresponding measurement signal when the modification or switching means outputs the first instruction signal and for outputting at least a selected one of the measurement signals when the modification or switching means outputs the second instruction signals, the selected measurement signal being modified or switched to have a level outside the corresponding range within which the level of the selected measurement signal varies in a normal state.

15. The oxygen concentration detection system as claimed in claim 14, further comprising judgment means for judging an anomaly of the oxygen concentration system based on a plurality of measurement signals of the sensor.

16. The oxygen concentration detection system as claimed in claim 14, further comprising memory means for storing data on kinds and locations of anomalies of the oxygen concentration detection system so that the oxygen concentration detection system makes anomaly judgments based on a plurality of the measurement signals and the stored data.

* * * * *